US012508393B2

(12) United States Patent
Rossen

(10) Patent No.: US 12,508,393 B2
(45) Date of Patent: Dec. 30, 2025

(54) PNEUMATIC MODULE AND PROCESS FOR SUPPLYING A CONSUMER WITH A PRESSURE SURGE-FREE STREAM OF MEDICAL GASES OR MEDICAL AIR

(71) Applicant: Drägerwerk AG & Co. KGaA, Lübeck (DE)

(72) Inventor: Thomas Rossen, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 774 days.

(21) Appl. No.: 17/470,040

(22) Filed: Sep. 9, 2021

(65) Prior Publication Data

US 2022/0072264 A1 Mar. 10, 2022

(30) Foreign Application Priority Data

Sep. 10, 2020 (DE) ..................... 10 2020 123 654.9

(51) Int. Cl.

*A61M 16/20* (2006.01)
*A61M 16/00* (2006.01)
*A61M 16/08* (2006.01)

(52) U.S. Cl.

CPC ...... *A61M 16/209* (2014.02); *A61M 16/0063* (2014.02); *A61M 16/08* (2013.01); *A61M 2205/3331* (2013.01)

(58) Field of Classification Search

CPC ............ A61M 16/209; A61M 16/0063; A61M 16/08; A61M 2205/3331; A61M 16/0078;

(Continued)

(56) References Cited

U.S. PATENT DOCUMENTS 4,224,940 A * 9/1980 Monnier ............. A61M 16/021 128/205.12
5,497,767 A * 3/1996 Olsson .................. A61M 16/00 128/205.13

(Continued)

FOREIGN PATENT DOCUMENTS

CN 86107539 A 7/1987
CN 1764486 A 4/2006

(Continued)

OTHER PUBLICATIONS

Murray Hinder, Alistair Mcewan, Thomas Drevhammer, Snorri Donaldson, Mark Brian Tracy,"T-piece resuscitators: how do they compare?", BMJ Journals, Apr. 18, 2018.

*Primary Examiner* — Justine R Yu
*Assistant Examiner* — Matthew R Moon
(74) *Attorney, Agent, or Firm* — McGlew and Tuttle, P.C.

(57) ABSTRACT

A pneumatic module (1) and a process supply a patient with breathing gas. An inlet (2) connects a medical gas source and an outlet (3) via a main flow duct (4) with a flow valve (5), setting a downstream volume flow, and a pressure relief valve (6) downstream of the flow valve (5) that vents the main flow duct (4) when a pressure is exceeded. A control duct (7), connected to a relief valve control port (8), branches off from the main flow duct (4) at a branch (15) upstream of the flow valve (5). A pressure control unit (9), arranged in the control duct, sets a flow value through the control duct (7), and acts on the control port (8) for setting a maximum pressure. The control port (8) is connected to a compensating element (10) providing a compensating volume (11) for the control duct (7).

14 Claims, 4 Drawing Sheets

(58) Field of Classification Search
CPC ...... A61M 2205/3341; A61M 2240/00; A61M 16/206; A61M 16/0003; A61M 16/01; A61M 16/0875; A61M 16/201; G05D 16/00
See application file for complete search history.

(56) References Cited

U.S. PATENT DOCUMENTS

| | | | | |
|---|---|---|---|---|
| 5,787,882 | A | 8/1998 | Hamilton | |
| 5,957,130 | A | 9/1999 | Krahbichler et al. | |
| 6,349,723 | B1 * | 2/2002 | Kock | A61M 16/01 128/203.14 |
| 7,992,555 | B2 * | 8/2011 | Heinonen | A61M 16/01 128/205.24 |
| 2006/0231098 | A1 * | 10/2006 | Downie | A61M 1/1698 128/204.22 |
| 2014/0021777 | A1 * | 1/2014 | Dinerman | B60T 15/36 137/488 |
| 2015/0059757 | A1 | 3/2015 | Sardesai et al. | |
| 2018/0369534 | A1 | 12/2018 | Bird | |

FOREIGN PATENT DOCUMENTS

| | | | | |
|---|---|---|---|---|
| CN | 201028046 | Y | 2/2008 | |
| CN | 111163828 | A | 5/2020 | |
| DE | 6604317 | U | 1/1970 | |
| DE | 2801546 | A1 | 7/1979 | |
| DE | 3104325 | A1 | 2/1982 | |
| DE | 239337 | A1 | 9/1986 | |
| DE | 3712388 | A1 | 10/1988 | |
| DE | 69621397 | T2 | 1/2003 | |
| DE | 102005039220 | B3 | 10/2006 | |
| DE | 102010004424 | A1 | 7/2011 | |
| GB | 1367599 | A * | 9/1974 | A61M 16/208 |

* cited by examiner

PNEUMATIC MODULE AND PROCESS FOR SUPPLYING A CONSUMER WITH A PRESSURE SURGE-FREE STREAM OF MEDICAL GASES OR MEDICAL AIR

CROSS REFERENCE TO RELATED APPLICATIONS

This application claims the benefit of priority under 35 U.S.C. § 119 of German Application 10 2020 123 654.9, filed Sep. 10, 2020, the entire contents of which are incorporated herein by reference.

TECHNICAL FIELD

The present invention pertains to a pneumatic module as well as to a process for supplying a consumer, which may be a laboratory device or a medical device, especially a breathing circuit connection element for a patient, with a medical gas and/or medical air from a gas source. An inlet for connection to the gas source and an outlet for connection to a hose line leading to the consumer are provided for this purpose. A main flow duct with a flow valve and with a pressure relief valve is located between the inlet and the outlet, so that both a constant volume flow and a maximum pressure prevailing in the main flow duct can be set. The maximum pressure, which causes, when it is reached or exceeded, the main flow duct to be ventilated (vented) at least from time to time through the pressure relief valve, can be set as needed via a suitable pneumatic actuation.

TECHNICAL BACKGROUND

In general, different applications, in which a laboratory device or a medical device, especially a breathing circuit connection element, e.g., a breathing mask or a tube, is supplied with a medical gas or with medical air, are known. If comparatively small volume flows of a medical gas or medical air are needed, as it happens, for example, during the ventilation of premature infants, the regulation of the corresponding gas or air supply must meet high requirements.

Ventilators as well as special ventilators, which can be used in neonatology, are generally known. Such ventilators may be configured as independent units or as modules, which are integrated into other devices, such as open care units or resuscitation units for newborn infants. DD 239 337 A1 describes in this connection a special pneumatic module, which is used during the automatic and manual ventilation of premature and newborn infants. The pneumatic module is arranged between a valve combination arranged close to the patient and a unit, arranged at a distance from the patient, for generating a breathing gas flow conditioned as needed, and which unit comprises a control unit, a breathing gas source, a heating element as well as a humidifying unit. Different modes of ventilation, including the high-frequency oscillatory ventilation, can be carried out by means of the pneumatic module described.

A ventilator, which provides a breathing gas stream for ventilating a toddler, is known, furthermore, from DE 28 01 546 A1. It is possible by means of the ventilator described to carry out a ventilation with different, specifically selectable ventilation modes, e.g., the PEEP process or the CPAP process, by means of the ventilator described.

Furthermore, open care units or resuscitation units for newborn infants are known, which make available a protected support surface for an infant, protect the patient from external effects, make thermotherapy possible and have a ventilator integrated in them at least partially. For example, the Resuscitaire® of Dräger, which has a ventilator and a pneumatic module for stimulating the intrinsic breathing in newborn infants, is known in this connection. The ventilation is carried out in patients whose breathing does not start automatically immediately after birth. The pneumatic module connects a gas or air source of the ventilator to a hose system, which does, in turn, establish a connection to a breathing circuit connection element, which is configured, e.g., in the form of a mask fixed over the mouth and the nose of the patient.

A pressure difference, which shall prevail in the ventilation system is set by the physician in case of the use of the above-described care units for ventilation. If the patient has no intrinsic breathing activity, a frequency, at which the ventilation strokes shall be carried out, is additionally set. The ventilation of the patient takes place between a lower pressure level, which is called PEEP (positive end-expiratory pressure) in ventilation, and an upper pressure level, called PIP (positive inspiratory pressure). The PEEP is here the pressure that becomes established at the end of the exhalation, while the PIP is reached at the end of the inhalation.

In reference to the prior-art pneumatic modules, especially for supplying newborn infants with medical gases and/or with medical air, there is, on the one hand, a need to carry out different types of ventilation, so-called ventilation modes, and, on the other hand, to make it possible to ensure the most accurate control or regulation possible of the properties of the breathing gas stream being delivered, comprising at least one medical gas and/or air, and here especially the volume flow and the pressure. This is of crucial significance above all in the case of the ventilation of newborn infants in order to prevent damage to the lungs, which have not developed fully at least partially.

The solutions known from the state of the art often meet the above-described requirements only partially. In particular, undesired deviations may develop, depending on the particular operating situation, between the pressures or pressure differences set by the operator and the pressures actually prevailing in the ventilation system. Such unintended, at times fluctuating pressure deviations, which occur, as a rule, only briefly, are due to the special mode of construction as well as to the actuation of the particular pneumatic final setting elements used. Since comparatively low ventilation pressures and pressure differences must be overcome precisely during the ventilation of infants, especially newborn and premature infants, even small pressure fluctuations of a few mbar account for a high percentage of the maximum pressure set, for example, of the PIP. This problem is explained, for example, in the publication "Hinder M., McEwan A., Drevhammer T. at al., T-Piece resuscitators: How do they compare?, Arch Dis Child Fetal Neonatal Ed, 2018: 0; F1-F6, doi 10.1136/archdischild-2018-314860" on the basis of a comparison of different pneumatic modules of this class.

SUMMARY

Based on the pneumatic modules known from the state of the art as well as the problems described above, a basic object of the present invention is to perfect a pneumatic module as well as a process for providing a stream of a medical gas and/or medical air such that a stream of the necessary medical gas or of the medical air, which is as free from pressure surges as possible, is made available to a consumer. The technical solution to be proposed should have a comparatively simple structural configuration and also should allow no or only slight deviations of the pressure in the breathing gas circuit from the predefined maximum pressure even in different operating situations, especially in case of use in emergency ventilation or in neonatal ventilation. Furthermore, a pneumatic module should be provided, which can generally be used in combination with different gas and/or air sources, and which can be integrated into both autarchically operating assembly units, conventionally configured ventilators and open care or resuscitation units for newborn infants. It is significant for this that the pneumatic module to be provided can be configured with prior-art structural elements and in a space-saving manner and the provided pneumatic module makes possible a failure-safe operation with a low maintenance requirement.

The above-described object is accomplished with a pneumatic module according to the invention and with a process according to the invention. Further, a special ventilation system for supplying a consumer with a medical gas and/or with medical air is described. Advantageous embodiments of the present invention are explained in more detail in the following description partly with reference to the figures.

The present invention pertains to a pneumatic module for supplying a patient with breathing gas, wherein breathing gas is defined in the sense of the present invention as a gas, gas mixture and/or air, which contains the medical gas or the at least one medical gas and/or medical air, wherein the supply with breathing gas is carried out basically as a gas supply supporting or replacing the natural breathing.

According to the present invention, the pneumatic module has an inlet for connecting a gas source for supplying a medical gas and/or medical air and an outlet for connecting a hose line leading to the patient. A main flow duct with a flow valve, at which a volume flow of a breathing gas stream flowing downstream of the flow valve can be set, and a pressure relief valve, which is arranged downstream of the flow valve and which is set up to vent the main flow duct at least from time to time when a permissible maximum pressure is exceeded, are provided between the inlet and the outlet. A control duct, which is connected to a control port of the pressure relief valve, branches off from the main flow duct upstream of the flow valve, wherein a pressure control unit, by which a flow value indicative of a control air flow flowing through the control duct and acting on the control port for setting the permissible maximum pressure can be set, is arranged in the control duct. The present invention is characterized in that the control port of the pressure relief valve is connected at least indirectly to a compensating element, which is configured to provide a compensating volume at least from time to time.

A compensating element for providing a compensating volume, which element is connected pneumatically to the control port of the pressure relief valve, is thus advantageously provided according to the present invention. It is possible due to such a compensating element, which is configured to provide a compensating volume at least from time to time as needed and rapidly, it is possible to absorb or to compensate effectively and without a time delay pressure fluctuations, especially pressure increases and the resulting movements of the air and displaced air volumes, which may develop on the actuation side of the pressure relief valve in the area of the control port when the maximum allowable pressure is reached or exceeded in the main flow duct. Pressure fluctuations, which are introduced into the control duct via the pressure relief valve when the maximum pressure set in the main flow duct is reached or exceeded, so that a feedback develops, can advantageously be reliably avoided or at least considerably reduced. The provision of a compensating element, which has a pneumatic connection to the control port, represents a comparatively simple structural solution here, which can be embodied with different means, which are both cost-effective and have a technically simple configuration.

Pressure surges, as they are known in pneumatic modules of this class, as they are known from the state of the art and may occur in certain operating situations, are reliably prevented from occurring with the solution according to the present invention. A laboratory device or medical device or a patient, especially a newborn or premature infant, who is connected at least indirectly to a pneumatic module configured according to the present invention, can be supplied in this manner with a pressure surge-free breathing gas stream reliably and continuously and thus in an especially safe manner.

Provisions are made in a special embodiment of the present invention for the compensating element to have at least one elastically deformable element, which is in a functional connection with the control port of the pressure relief valve at least indirectly. It is especially advantageous if the elastically deformable element is connected pneumatically to the control port, so that there is a gas- and air-tight flow duct between the control port and the elastically deformable element, in which the compensating volume is located. It is especially advantageous in this connection if the section between the control port and the compensating element is short and/or a flow resistance of the flow duct between the control port and the compensating element is low, so that pressure fluctuations, especially pressure increases, within the control duct can be rapidly reduced.

If the maximum pressure, the PIP during a ventilation, which is desired by the operator and is set correspondingly, is reached or exceeded in the main flow duct, the min flow duct is vented by the pressure relief valve at least from time to time and the overpressure is thus reduced or the pressure in the main flow duct is maintained at a constant level until the pressure drops again below the predefined maximum pressure. Pressure surges possibly occurring in the area of the control port during the ventilation process on the actuation side of the pressure relief valve and air volumes, which are additionally displaced hereby, are absorbed by an increase of the interior space of the elastically deformable compensating element.

The compensating element preferably has the shape of an ellipsoid of revolution or a sphere and is especially preferably configured as an elastic balloon or bellows, preferably as an expansion bellows. An elastic balloon, which has a diameter of 31 mm to 33 mm, especially about 32 mm at a location with a maximum extension and a diameter of 11 mm to 13 mm and especially about 12 mm at a location with minimum expansion, may also be used instead of an expansion bellows.

The wall thickness of the compensating element is preferably in a range of 0.25 mm to 0.35 mm, preferably about 0.3 mm. A silicone or rubber material is preferably suitable for use as an elastic material. It is advantageous to select a material with a Shore hardness of about 50.

It is essential for the selection of the material and for the configuration of the compensating element that this should absorb pressure surges occurring in the control duct without delay and as completely as possible, on the one hand, and that it should not be too elastic, on the other hand, in order to prevent its rapid filling until the necessary control pressure is reached, especially at the time of putting the pneumatic module into operation.

To make it possible to set the maximum pressure desired in the main flow duct, a pressure control unit, by which the pressure prevailing in the control duct and/or acting on the control port of the pressure relief valve can be changed in a specific manner and as needed, is provided in the control duct. The control air stream flowing through the control duct flows advantageously via an outlet of the control duct against atmospheric pressure into the surrounding area. According to a special embodiment of the present invention, provisions are made for the pressure control unit to have a flow valve, at which a volume flow of the control air stream flowing downstream of the flow valve can be set. It is possible by means of such a flow valve to set the volume flow of the control air stream in a specific manner and thus also to preset the pressure in the control duct as a function of a constant or variable flow resistance of the control duct and/or of inserts thereof.

The pressure control unit preferably has at least one element with a constant or variable flow resistance for setting the pressure acting on the control port of the pressure relief valve. In an especially suitable configuration, the pressure control unit of the control duct has a setting element, whose flow resistance can be set. Another special variant makes provisions for the pressure control unit having a flow valve, at which a volume flow of the control air stream flowing downstream of the flow valve can be set, and at least one element arranged downstream of the flow valve with constant or variable flow resistance.

The pressure control unit is always set up such that an operator sets the control pressure prevailing in the control duct as a function of the maximum pressure desired for the main flow duct, which corresponds, for example, to the PIP. It is advantageously conceivable in this connection that the volume flow of the control air stream is set by the operator at a constant value and the control air stream finally flows through an outlet of the control duct against the atmospheric pressure into the surrounding area. The control pressure prevailing within the control line and hence the maximum pressure predefined for the main flow duct depend on the volume flow of the control air stream and the flow resistance of the control duct outlet as well of the control duct and possible inserts, which are arranged upstream of the control duct outlet. The change in the control pressure may be brought about now by means of the pressure control unit by either the volume flow of the control air stream being changed while the flow resistance in the control duct remains constant at the same time or else by the volume flow being maintained at a constant level, while the flow resistance is changed in a specific manner. An essential feature of the pressure control unit is in either case that the pressure prevailing in the control duct and hence at the control port can be set in a specific manner and accurately by the operator.

The pressure control unit therefore has suitable pneumatic components for changing the volume flow of the control air stream and/or for setting the flow resistance of the control duct, including the outlet thereof, as needed. It is conceivable in this connection that the pressure control unit has, upstream of the control duct outlet, at least one flow valve for specifically setting and changing a volume flow and/or at least one element with constant or variable flow resistance. The present invention also pertains, furthermore, to a ventilation system for supplying a patient with a breathing gas, which has at least one medical gas and/or medical air. The ventilation system has a gas source, which preferably has a compressor, for providing a stream of a medical gas and/or medical air at a device outlet, a hose system, via which the breathing gas stream can be fed at least partially to the patient, and a pneumatic module, which is configured according to at least one of the above-described embodiments and which is connected at least indirectly to the device outlet and to an inlet of the hose system. A ventilation system configured according to the present invention is thus characterized by the use of a specially configured pneumatic module. Such a ventilation system can be embodied by means of a ventilator, which can provide different ventilation modes, or it may be a part of an open care or resuscitation unit for newborn infants in order to supply these with the necessary breathing gas stream immediately after birth.

The present invention also pertains, furthermore, to a process for supplying a consumer, especially a laboratory device or a medical device, which may be, e.g., a patient connection piece, such as a breathing mask or a tube, with a pressure surge-free stream of a medical gas and/or medical air. The present invention thus pertains to a process for preventing unintended pressure surges within a main flow duct, which connects a source for a medical gas and/or for medical air to a consumer. A stream of a medical gas and/or medical air is provided here at an inlet and a second part of this gas and/or air stream is sent in a main flow duct to a flow valve, via which a volume flow or a gas and/or air stream flowing downstream of the flow valve, which stream is also called breathing gas stream, is set. Further, the main flow duct is vented by means of a pressure relief valve at least from time to time when a predefined maximum pressure is exceeded, so that the maximum pressure is not exceeded in the main flow duct. A second part of the gas and/or air stream provided at the inlet is branched off upstream of the flow valve into a control duct and is sent in the control duct to a pressure control unit, by means of which a flow value indicative of a control flow flowing through the control duct and acting on a control port of the pressure relief valve for setting the permissible maximum pressure is set. It is essential that the control pressure prevailing in the control duct is set by means of this action at a value, so that the main flow duct is vented at least briefly when the desired maximum pressure is reached or exceeded. The process is characterized according to the present invention in that pressure surges, i.e., air displaced briefly additionally, which occur at the control port of the pressure relief valve, are absorbed and thus equalized in a compensating volume, which is generated by an at least partial elastic deformation of a compensating element, which is connected at least indirectly to the control port. A flow duct, which is preferably short and has a low flow resistance, is advantageously arranged between the control port and the compensating element.

An essential feature of the process described is that a compensating volume, which is preferably in a direct pneumatic connection with the control port, is provided as needed at least from time to time on the control side of the pressure relief valve. The flow resistance between the control port and the equalization is such that at least a part of the control air acting on the control port is displaced in the direction of the compensating volume during a brief and rapid pressure rise. The development of pressure peaks on the control side of the pressure relief valve, which would ultimately lead, in turn, to unintended pressure peaks within the main flow duct, is thus advantageously prevented.

In a special embodiment of the present invention, a volume flow of the control flow flowing through the control duct, which flow exerts a force on the control port of the pressure relief valve, is set at the pressure control unit arranged in the control duct as a function of the permissible maximum pressure desired in the main flow duct. The operator thus sets a volume flow for the control flow in the pressure control unit as a function of the maximum pressure desired in the pressure control unit. Furthermore, provisions are advantageously made for the control flow flowing through the control duct to be released via an outlet into a surrounding area against the atmospheric pressure prevailing in the surrounding area. Depending on the flow resistance within the control duct and the volume flow of the control flow, a control pressure, which acts on the control port of the pressure relief valve, becomes established within the control duct. In order to specifically set a desired pressure within the control duct, it is, furthermore, advantageous to arrange in the control duct, upstream of the outlet, an element. which has a non-adjustable flow resistance, or else a setting element, whose flow resistance can be varied in a specific manner. It is advantageously possible by providing a corresponding element upstream of the outlet within the flow duct to increase the pressure within the control duct either by increasing the volume flow of the control flow at constant flow resistance or else by specifically increasing the flow resistance at a setting element at constant volume flow. It is always essential that the pressure can be set by an operator within the control duct such that the desired maximum pressure will not be exceeded in the main flow duct.

As soon as the predefined maximum pressure is reached or exceeded in the main flow duct, the main flow duct is vented via the pressure relief valve. Based on the compensating volume provided according to the present invention within the control duct, a pressure surge-free delivery of a stream of medical gas and/or medical air is ensured as well when the maximum pressure is reached in the main flow duct and due to the ventilation operation brought about hereby. In particular, a feedback of pressure peaks in the control duct to the pressure prevailing in the main flow duct is prevented with certainty.

Provisions are, furthermore, made in a very special embodiment of the process according to the present invention for the pressure surge-free stream of a medical gas and/or medical air to be fed to a laboratory apparatus and/or to a medical device. It is expressly pointed out in this connection that a medical device is preferably a breathing circuit connection piece of a patient, especially a breathing mask, nasal prongs or a tube. It is likewise conceivable that the pressure surge-free stream of a medical gas and/or medical air, which is achieved according to the present invention, is fed to a laboratory device or to another medical device and additional processing, procedural and/or process steps are carried out with the gas stream and/or air stream.

The present invention will be explained in more detail below without limitation of the general inventive idea on the basis of special exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
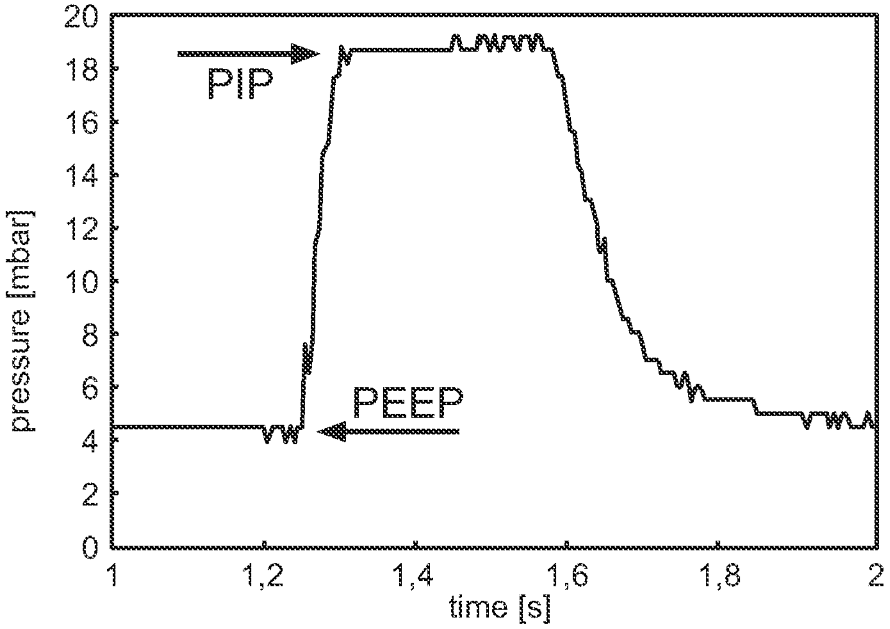
FIG. 1 is a graph showing a pressure curve (pressure course) during a ventilation cycle.

Referring to the drawings, FIG. 1 shows the pressure curve during a ventilation cycle of a ventilated patient. Such a ventilation may be carried out, for example, with an open care or resuscitation unit for newborn infants, which is carried out above all when the breathing of the newborn infant does not begin spontaneously immediately after birth.

The ventilator of the care unit is connected via a hose system to a patient connection piece, especially a breathing mask, which is pressed over the mouth and the nose of the patient. To carry out the ventilation, the desired pressure difference is set by an operator, and the frequency for the recurrence of the ventilation cycles can be set as well.

As is shown in FIG. 1, the pressure difference is between a lower pressure, conventionally called PEEP (positive end-expiratory pressure) in ventilation, as well as an upper pressure, usually called PIP (positive inspiratory pressure). The PEEP is the pressure that becomes established at the end of the exhalation, whereas the PIP is reached at the end of the inhalation. FIG. 1 shows the pressure curve for a complete ventilation cycle, in which the two pressure levels PEEP and PIP are marked.

The breathing gas stream is delivered by the ventilator independently from the current phase of the ventilation cycle. An exhalation valve, through which air exhaled by the patient can escape, is closed at the beginning of the inhalation, so that the lungs of the patient will be filled with the breathing gas stream being delivered by the ventilator, until the PIP is reached. When this pressure level is reached, the main flow duct leading to the patient is ventilated, as it will be explained in even more detail below, so that the PIP, which is in this case the maximum pressure predefined by the operator in the main flow duct, in the hose system connected thereto and in the lungs of the patient, is maintained at a constant value until the exhalation of the breathing gas contained in the lungs takes place via the exhalation valve.

Figure 2:
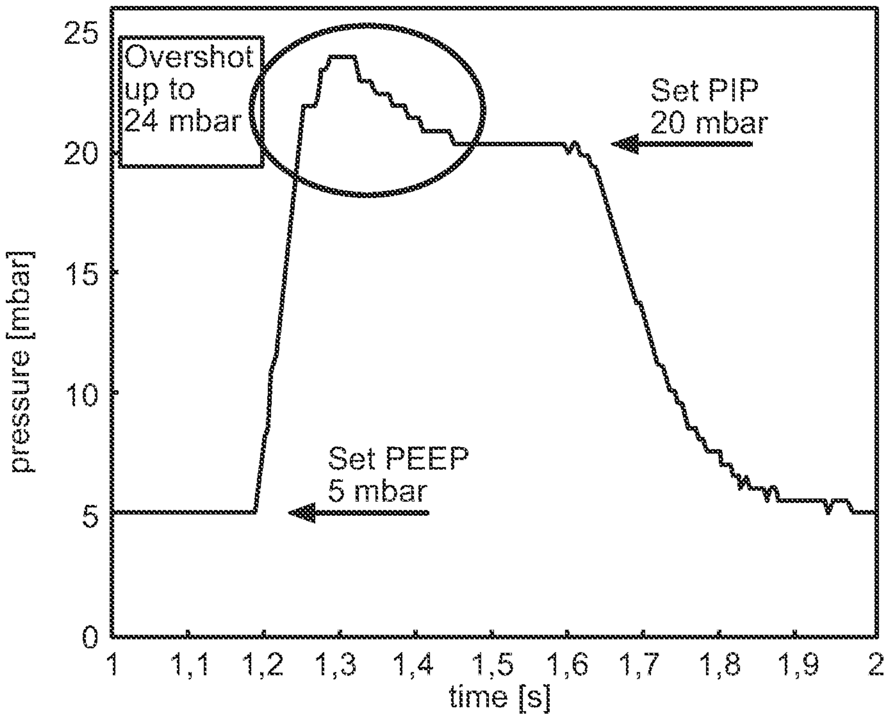
FIG. 2 is a graph showing a view of an overshooting of the pressure curve during the inhalation phase of a ventilation cycle.

In addition to the view according to FIG. 1, FIG. 2 shows a view of a ventilation cycle, in the course of which an unintended overshooting of the pressure occurs, which leads to an overshooting of the maximum pressure set by the operator, here the PIP. According to the exemplary embodiment shown in FIG. 2, a PEEP of 5 mbar and a PIP of 20 mbar were set. Shortly after reaching the PIP, which should not ideally be exceeded, there is an increase in the pressure in the main flow duct to a value of 24 mbar and hence to the set maximum pressure being exceeded by 20% relative to the desired pressure difference. The development of pressure surges during the supply of a stream of medical gas and/or medical air is prevented by the use of a pneumatic module configured according to the present invention as well as of a corresponding process.

Figure 3:
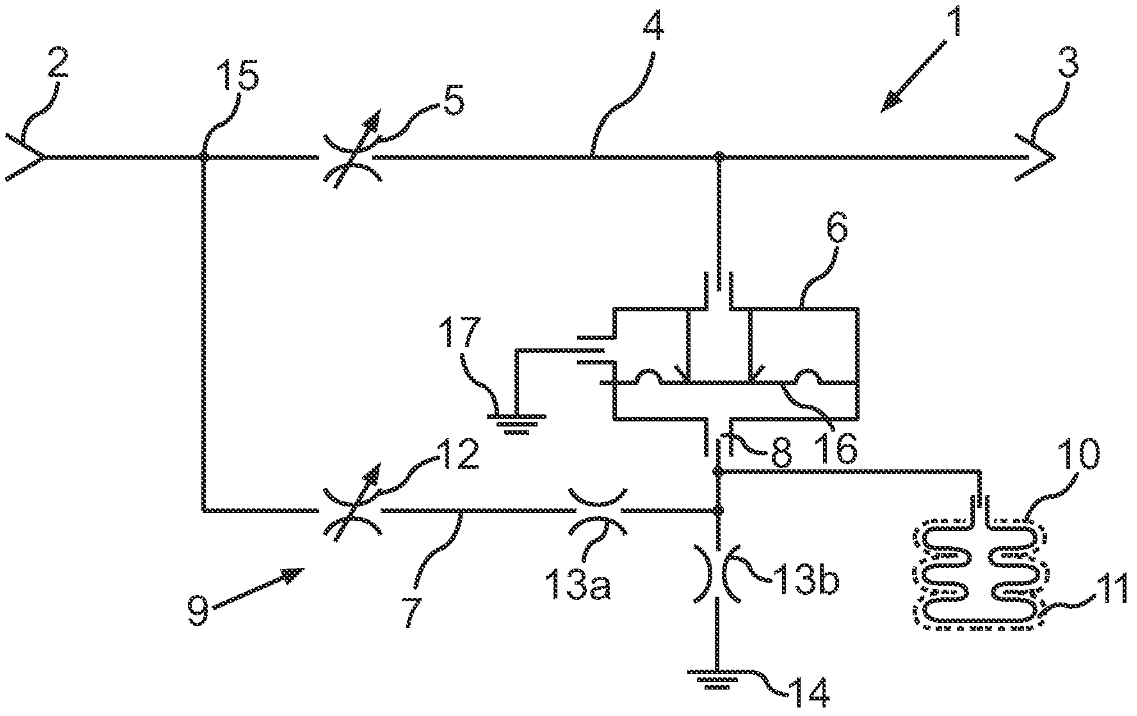
FIG. 3 is a pneumatic circuit diagram of a first variant of a pneumatic module configured according to the present invention with a compensating element according to a first embodiment.
Figure 7:
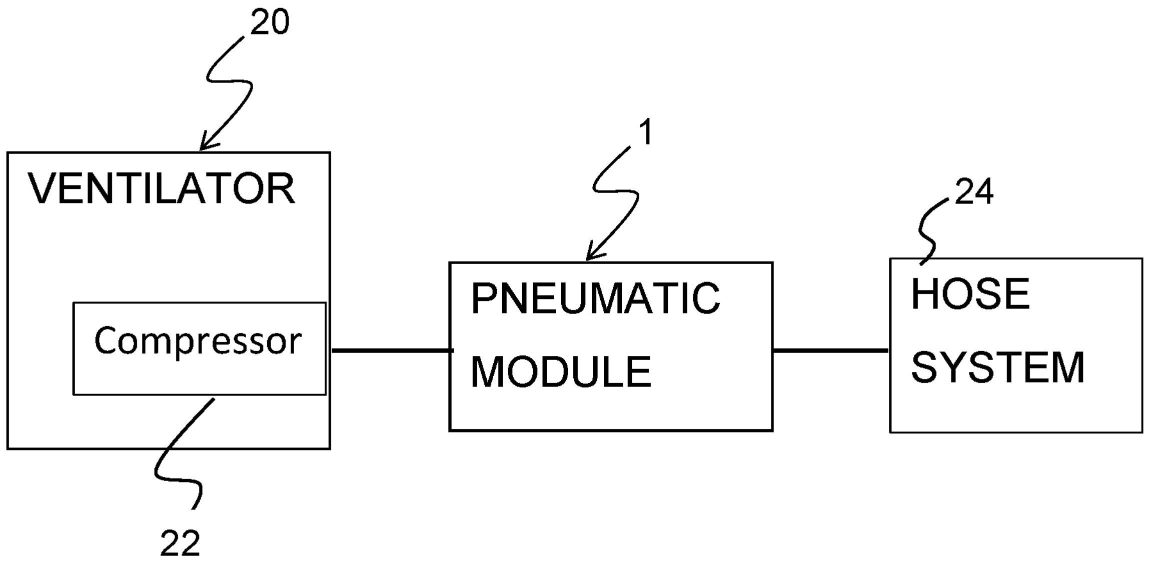
FIG. 7 is a schematic view showing a ventilation system for supplying a patient with a breathing gas.

FIG. 3 shows a pneumatic circuit diagram of a pneumatic module 1 configured according to the present invention. The pneumatic module 1 is supplied with a stream of medical gas and/or medical air from a gas or air source. Such a gas or air source may be both a compressor of a ventilator 20 or anesthesia apparatus, a pressurized gas cylinder or a central hospital supply system for medical gases and medical air. FIG. 7 shows the ventilator 20 with the compressor 22.

A stream of medical gas and/or medical air, which will hereinafter be called breathing gas stream in a simplified manner, flows via an inlet 2 into a main flow duct 4 of the pneumatic module 1. A flow valve 5, at which the desired volume flow of the breathing gas stream can be set by an operator, is arranged first in the main flow duct 4. The breathing gas stream flows with the constant volume flow through the main flow duct 4, which is usually a part of a hose system 24 or is connected to this hose system 24, to the patient connection piece, for example, to a breathing mask, which is pressed over the mouth sand the nose of the patient.

The breathing gas stream flows steadily through the main flow duct 4 independently from the current phase of the ventilation cycle. If the patient is inhaling, the outlet is closed at an exhalation valve, not shown here, via which the patient can exhale, so that the breathing gas stream completely enters the lungs of the patient being ventilated. The lungs will fill during this phase of the ventilation cycle until the maximum pressure of the PIP set by the operator is reached. If this pressure level is reached, the main flow duct 4 is vented via the pressure relief valve 6 connected pneumatically to the main flow duct 4. It is ensured in this manner that the pressure in the main flow duct 4 and hence at the patient will not rise above the maximum pressure set by the operator, the PIP.

In order to make it possible to set the maximum pressure prevailing in the main flow duct 4, here the PIP, as needed, a control is provided, which will be explained in more detail below.

A control duct 7 branches off from the main flow duct 4 at a branch 15 upstream of the flow valve 5, and a pressure control unit 9, with which a control pressure within the control duct 7, especially at the control port 8 of the pressure relief valve 6, can be set in a specific manner, is located downstream of this branch 15. According to the configuration space shown in FIG. 3, the pressure control unit 9 has a flow valve 12, with which the operator can set a control flow, here a control air flow, in a specific manner with a constant volume flow, as well as two flow resistance elements 13*a*, 13*b* with suitably selected flow resistance. The control flow flows during the operation of the pneumatic module 1 through an outlet 14 out of the control duct 7 into the surrounding air and hence against the ambient or atmospheric pressure prevailing in the surrounding area.

In terms of the technical configuration and its functionality, the flow valve 12 arranged in the control duct 7 corresponds to the flow valve 5 arranged in the main flow duct 4, but the volume flow of the control flow is markedly lower than that of the breathing gas stream in the main flow duct 4. The ratio of the volume flows of the control flow to the breathing gas flow is usually 1:10 in the exemplary embodiment being explained here.

In the flow direction between the flow valve 12 and the outlet 14, the pressure control unit 9 has two flow resistances 13*a*, 13*b* arranged in the control duct 7. By a suitable selection, alternatively setting of the flow resistances 13*a*, 13*b*, it is possible to set in a specific manner a control pressure, which prevails within the control duct 7 and acts on the control port 8 of the pressure relief valve 6 while setting at the same time a defined volume flow for the control flow.

According to the embodiment shown in FIG. 3, the pressure relief valve 6 is a diaphragm valve, where the diaphragm 16 pneumatically separates the main flow duct 4 from the control duct 7. A movement of the diaphragm 16 therefore takes place as a function of the pressures present on both sides, i.e., the pressure in the main flow duct 4 as well as the control pressure. If the pressure in the main flow duct 4 exceeds the control pressure and hence the maximum pressure desired by the operator, here the PIP, the diaphragm is deflected such that the main flow duct 4 is vented via a ventilation opening 17 of the pressure relief valve 6 as long as this operating state persists, so that the pressure in the main flow duct 4 remains constant.

If the operator increases, for example, the volume flow of the control flow, the control pressure rises within the control duct 7 and so does the maximum pressure predefined for the main flow duct 4. The operator can set in this manner the control pressure and hence the predefined maximum pressure, here the PIP, in a continuously adjustable manner.

As soon as the pressure prevailing in the main flow duct 4 exceeds the maximum pressure preset by the operator, a movement of the diaphragm 16 of the pressure relief valve 6 takes place, as was described before, in the direction of the control duct 7. Based on this movement, a gas or air volume in the area of the control port 8 in the control duct 7 must be displaced corresponding to the movement of the diaphragm 16. Without the compensating element 10 provided according to the present invention, which provides a compensating volume 11 connected pneumatically to the control port 8, the gas or air volume additionally displaced in the control duct 7 by the diaphragm 16 would have to be released via the outlet 14 of the control duct 7 into the surrounding area against the existing flow resistances and the prevailing atmospheric pressure. Due to the existing flow resistances, especially the second flow resistance element 13*b* arranged between the control port and the outlet, an increase in the control pressure in the control duct 7, which increase acts, in turn, on the control port 8 and on the diaphragm 16 of the pressure relief valve 6, is fed back into the main flow duct 4. This feedback would ultimately lead again to an increase in the pressure in the main flow duct 4 above the maximum pressure preset by the operator, i.e., the PIP.

In order reliably to prevent such an unintended increase in the pressure in the main flow duct 4 above the maximum pressure set, a compensating element 10 with an elastic wall, by which a compensating volume connected pneumatically to the control port 8 is made available as needed, is provided in the control duct 7. The flow resistance between the control port 8 of the pressure relief valve 6 and the compensating element 10 is configured here to be so small that when the set maximum pressure is reached in the main flow duct 4, the air volume additionally displaced on the actuation side of the pressure relief valve 6 can be absorbed directly and rapidly by the compensating volume 11 and it does not have to be removed via the outlet 14 of the control duct 7 into the surrounding area. Based on this technical measure, an overshooting of the pressure in the main flow duct 4 above the set maximum pressure is reliably and rapidly prevented from occurring.

An essential advantage of the solution according to the present invention over a likewise conceivable solution, which provides for a reduction, at least from time to time, of the flow resistances present between the control port 8 of the pressure relief valve 6 and the outlet 14 in the flow duct 7, especially of the flow resistance of the second flow resistance element 13*b*, is that the volume flow of the control flow would be greater in this alternative solution during the normal operation at equal control pressure, which would, on the whole, increase the consumption of medical gas and/or medical air. The technical solution according to the present invention can thus be implemented in a technically comparatively simple manner and it also represents an economically meaningful solution.

It is essential for the configuration of the compensating element 10 for providing from time to time a compensating volume 11 in the control duct 7 that this is, on the other hand, so elastic that a gas or air volume additionally displaced in the control duct 7 can be absorbed rapidly and completely, and, on the other hand, it is not so elastic that the filling of the control duct 7 and the reaching of the desired control pressure at the start-up of the pneumatic module 1 would last too long not to be ready for use rapidly in an emergency. The compliance of the compensating element 10, which is a value indicative of an increase in volume as a function of a pressure increase acting from the inside, is configured therefore such that the above-described boundary conditions are taken into account.

The compensating element 10 is configured as an expansion bellows made of silicone in the embodiment described in connection with FIG. 3, wherein the folds have a uniform configuration and are arranged symmetrically in relation to a central axis of the expansion bellows. This compensating element 10 is suitable for operation in a pneumatic module 1, which can also be used in emergencies. The compliance of the expansion bellows is selected here to be such that the displaced volume developing in certain cases of operation in the control duct 7 can be absorbed rapidly and completely, and rapid filling of the compensating volume 11 provided additionally is ensured when the pneumatic module 1 is put into operation.

Figure 4:
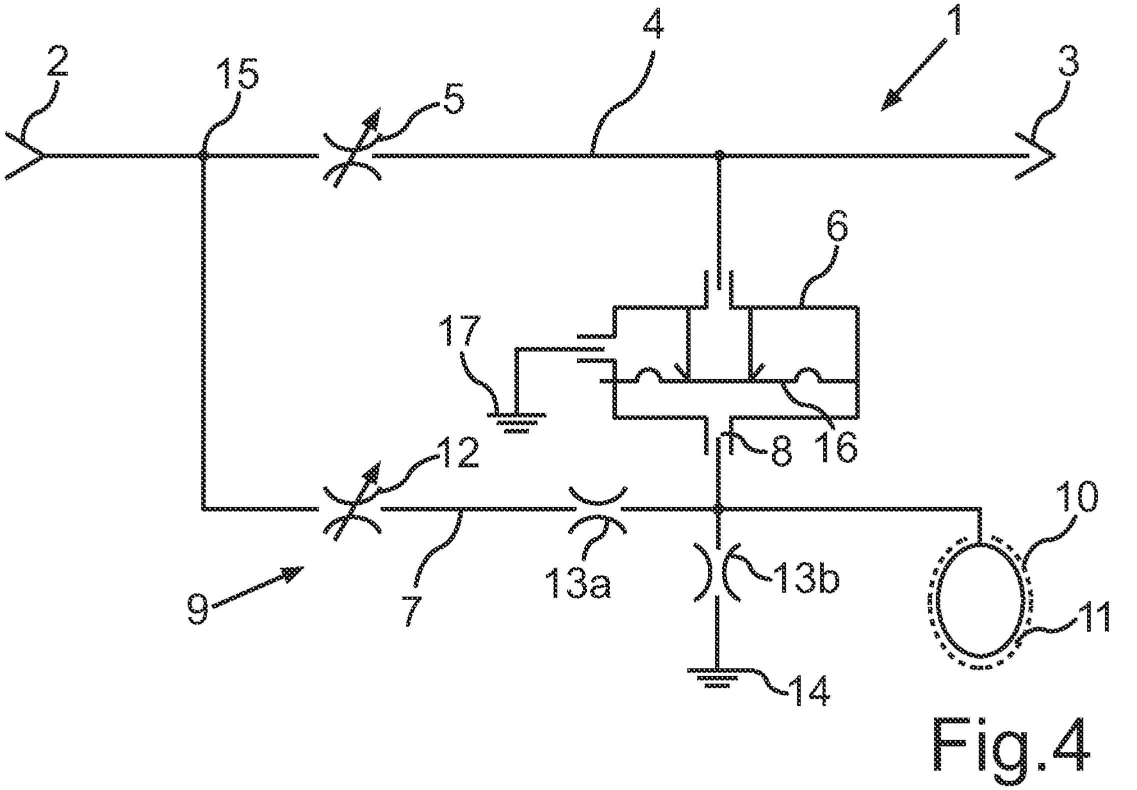
FIG. 4 is a pneumatic circuit diagram of a first variant of a pneumatic module configured according to the present invention with a compensating element according to a second embodiment.

FIG. 4 shows a pneumatic circuit diagram of a special embodiment of a pneumatic module 1, which is configured according to the present invention and which thus likewise has an additional compensating element 10, which provides a compensating volume 11 for the control duct 7 as needed. The pneumatic configuration of the pneumatic module 1 corresponds here to that which was described in connection with FIG. 3. Contrary to the pneumatic module 1 according to FIG. 3, the compensating element 10 is not, however, configured in the form of an elastic balloon with a flat balloon wall. It is conceivable in this case to likewise use silicone or a suitable rubber material for the compensating element 10. It is essential again that the compliance of the compensating element 10 is selected to be such that a rapid and immediate absorption of the displaced volume developing in the control duct 7 in certain operating situations is ensured, on the one hand, and full readiness to operate is established as rapidly as possible when putting the pneumatic module 1 into operation, on the other hand.

Figure 5:
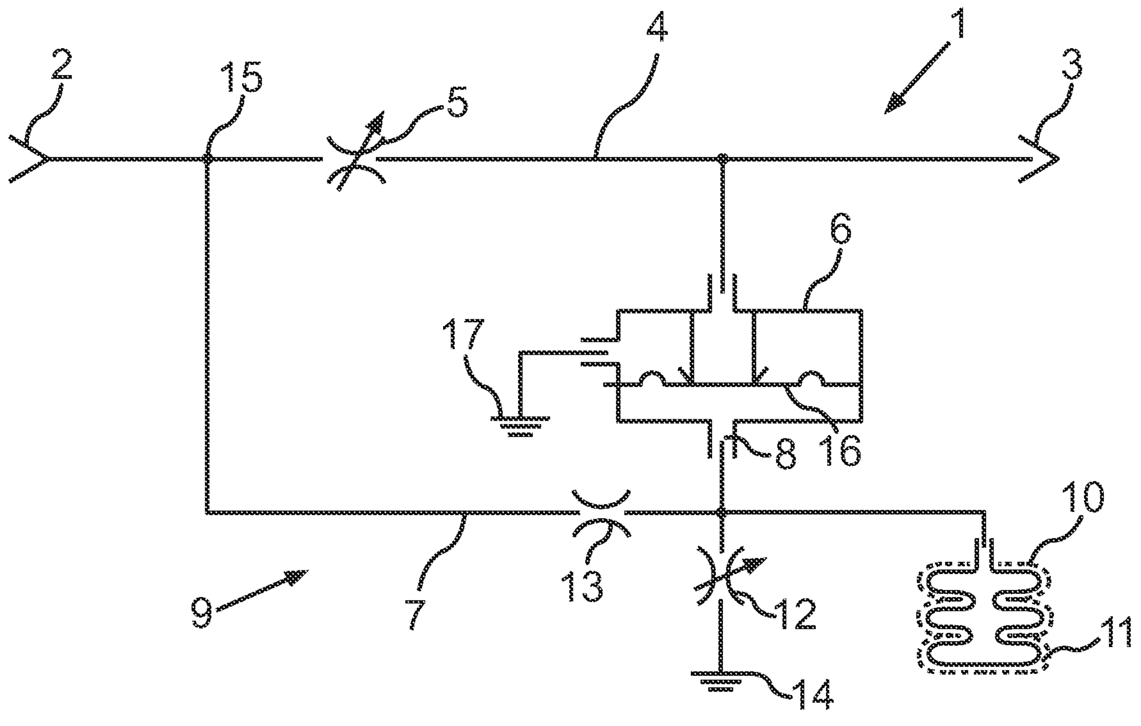
FIG. 5 is a pneumatic circuit diagram of a second variant of a pneumatic module configured according to the present invention with a compensating element according to the first embodiment.

The pneumatic module 1, whose pneumatic circuit diagram is shown in FIG. 5, differs from the pneumatic modules 1 described before by an alternatively configured pressure control unit 9 in the control duct 7. According to the exemplary embodiment shown in FIG. 5, the pressure control unit 9 has a flow resistance element 13 with a constant, alternatively variable flow resistance and a flow valve 12, which is arranged downstream of the flow resistance element 13 in front of the outlet 14 of the control duct 7, via which an operator can set a volume flow of the control flow.

Depending on the volume flow upstream of the flow resistance element 13 and of the flow resistance of the flow resistance element 13, a control flow with constant volume flow becomes established upstream of the flow valve 12. By actuating the flow valve 12, this volume flow and at the same time the control pressure prevailing within the flow duct 7 can be changed. The control pressure set by the operator in this manner is present, in turn, at the control port 8 of the pressure relief valve 6, so that the maximum pressure, here the PIP, can be set in the main flow duct 4 by setting the flow valve 12 in a suitable manner.

A compensating element 10, in the form of an expansion bellows according to the embodiment described, which is pneumatically connected to the control port 8 of the pressure relief valve 6, is provided in turn according to the present invention. The compensating volume 10 is dimensioned such that when necessary, especially when the permissible maximum pressure is reached or exceeded in the main flow duct 4, i.e., when the main flow duct 4 is vented via the pressure relief valve 6, it can rapidly and fully absorb the gas or air volume displaced additionally in the area of the control port 8 in the control duct 7.

Figure 6:
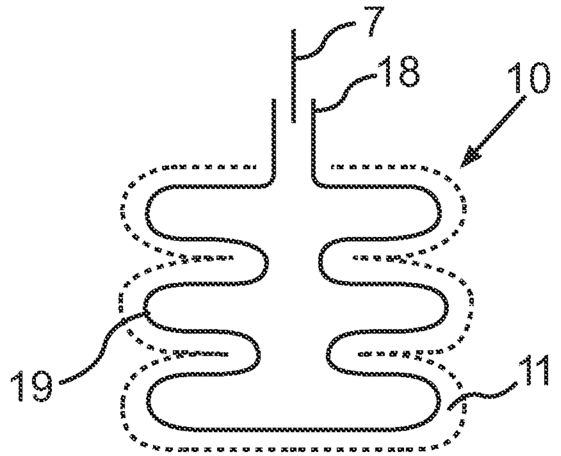
FIG. 6 is a schematic detail view of an expansion bellows, which can be used for a pneumatic module configured according to the present invention.

FIG. 6 shows a specially configured elastic compensating element 10, which can provide in its interior a compensating volume 10 at least from time to time based on an expansion of its outer wall. A gas or air volume displaced additionally in the control duct 7 over a short time period is absorbed according to the present invention in the compensating volume 11 of the compensating element 10 in certain operating situations.

The compensating element 10 shown is configured as an expansion bellows made of silicone. The compensating element 10 has a port 18 in the upper area in order to connect this compensating element pneumatically at least indirectly to the control port 8 of a pressure relief valve 6. Furthermore, the compensating element 10, here the expansion bellows, has a plurality of folds 19, three folds in this case, which have all a uniform configuration and are arranged symmetrically in relation to a central axis of the expansion bellows. The expansion bellows shown makes possible a rapid and complete absorption of the gas or air volume displaced additionally in certain operating situations in a control duct 7 of a pneumatic module 1 configured according to the present invention. The compliance of the expansion bellows, i.e., the ratio of the volume enlargement to the pressure increase, is selected to be such that the gas or air volume displaced additionally can be absorbed rapidly and completely, on the one hand, and, on the other hand, that filling of the compensating element 10 takes place so rapidly when a pneumatic module 1 is put into operation that a pneumatic module 1 configured according to the present invention can be used for emergency ventilation.

While specific embodiments of the invention have been shown and described in detail to illustrate the application of the principles of the invention, it will be understood that the invention may be embodied otherwise without departing from such principles.

LIST OF REFERENCE NUMBERS

1 Pneumatic module
2 Inlet
3 Outlet
4 Main flow duct
Flow valve
6 Pressure relief valve
7 Control duct
8 Control port
9 Pressure control unit
Compensating element
11 Compensating volume
12 Flow valve in the control duct
13 Flow resistance element
13*a* First flow resistance element
13*b* Second flow resistance element
14 Outlet of the control duct
15 Branch
16 Diaphragm
17 Ventilation opening
18 Port of the compensating element
19 Fold
20 Ventilator
22 Compressor
24 Hose system

What is claimed is:

1. A pneumatic module for supplying a patient with breathing gas, the pneumatic module comprising:

an inlet for connecting a gas source for providing a medical gas and/or medical air;

an outlet for connecting a hose line leading to the patient;

a main flow duct from the inlet to the outlet;

a flow valve connected to the main flow duct and configured to set a volume flow of a breathing gas stream flowing downstream of the flow valve;

a pressure relief valve pneumatically connected to the main flow duct downstream of the flow valve and configured to vent the main flow duct upon a pressure in the main flow duct exceeding a permissible maximum pressure, the pressure relief valve having a control port;

a control duct connected to the control port and branching off from the main flow duct at a branch upstream of the flow valve;

a pressure control unit connected to the control duct and configured to set a flow value, indicative of a control flow, which flows through the control duct and which acts on the control port, for setting the permissible maximum pressure; and a compensating element configured to provide a compensating volume for the control duct, wherein the control port is connected to the compensating element, the compensating element comprising an elastically deformable element at least indirectly functionally connected with the control port, the elastically deformable element comprising an elastic expansion bellows, the compensating element being configured to receive fluid from the control port, wherein the control flow is released from the control duct via a control duct outlet into a surrounding area under the control port, the control port, the compensating element and the control duct outlet being located on one side of the pressure relief valve.

2. A pneumatic module in accordance with claim 1, wherein the compensating element is pneumatically connected to the control port.

3. A pneumatic module in accordance with claim 2, wherein the control port is in fluid communication with the control duct.

4. A pneumatic module in accordance with claim 1, wherein the pressure control unit comprises a flow valve configured to set a volume flow of the control flow flowing downstream of the flow valve.

5. A pneumatic module in accordance with claim 1, wherein the pressure control unit comprises:

a flow valve, at which a volume flow of the control flow flowing downstream of the flow valve can be set.

6. A ventilation system for supplying a patient with a breathing gas, the ventilation system comprising:

a ventilator comprising a compressor for providing an air and/or gas stream at a ventilator outlet;

a hose system configured to feed the air and/or gas stream at least partially to a patient; and a pneumatic module comprising:

a module inlet connected at least indirectly to the ventilator outlet:

a module outlet connected to a hose system inlet of the hose system;

a main flow duct from the module inlet to the module outlet;

a flow valve connected to the main flow duct and configured to set a volume flow of a breathing gas stream flowing downstream of the flow valve;

a pressure relief valve pneumatically connected to the main flow duct downstream of the flow valve and configured to vent the main flow duct upon a pressure in the main flow duct exceeding a permissible maximum pressure, the pressure relief valve having a control port;

a control duct connected to the control port and branching off from the main flow duct at a branch upstream of the flow valve;

a pressure control unit connected to the control duct and configured to set a flow value, indicative of a control flow, which flows through the control duct and which acts on the control port, for setting the permissible maximum pressure; and a compensating element configured to provide a compensating volume for the control duct, wherein the control port is connected to the compensating element, the compensating element comprising an elastically deformable element at least indirectly functionally connected with the control port, the elastically deformable element comprising an elastic expansion bellows, the compensating element being configured to receive fluid from the control port, wherein the control duct comprises a control duct outlet downstream of the pressure control unit, via which the control flow can be released into a surrounding area under an atmospheric pressure prevailing in the surrounding area, the compensating element being connected to the control duct at a position located between the control duct outlet and the control port, the compensating element, the control port and the outlet being located on one side of the pressure relief valve.

7. A ventilation system in accordance with claim 6, wherein the compensating element is pneumatically connected to the control port.

8. A ventilation system in accordance with claim 7, wherein the control port is in fluid communication with the control duct.

9. A ventilation system in accordance with claim 6, wherein the pressure control unit comprises a flow valve configured to set a volume flow of the control flow flowing downstream of the flow valve.

10. A ventilation system in accordance with claim 6, wherein the pressure control unit comprises:

a flow valve, at which a volume flow of the control flow flowing downstream of the flow valve can be set.

11. A process for supplying a consumer with a pressure surge-free stream of a medical gas and/or medical air, the process comprising the steps of:

providing a stream of a medical gas and/or medical air into a main flow duct at an inlet of the main flow duct;

sending a first part of the stream of a medical gas and/or medical air in the main flow duct to a flow valve, via which a volume flow of a breathing gas stream flowing downstream of the flow valve is set;

venting the main flow duct by means of a pressure relief valve upon a permissible maximum pressure being exceeded; and branching off a second part of the provided stream of a medical gas and/or medical air into a control duct upstream of the flow valve and sending the second part of the provided stream of a medical gas and/or medical air in the control duct to a pressure control unit configured to set a flow value indicative of a control flow, which flows through the control duct and acts on a control port of the pressure relief valve for setting the permissible maximum pressure compensating or absorbing pressure surges and air and/or gas volumes displaced thereby, which occur at the control port of the pressure relief valve, in a compensating volume, which is generated by an at least partially elastic deformation of a compensating element, which compensating element is operatively connected to the control port, the compensating element comprising an elastically deformable element at least indirectly functionally connected with the control port, the elastically deformable element comprising an elastic expansion bellows, the compensating element being configured to receive fluid from the control port, wherein the control flow is released from the control duct via an outlet into a surrounding area under an atmospheric pressure prevailing in the surrounding area, the compensating element being connected to the control duct at a position located between the outlet and the control port, the control port, the compensating element and the outlet being located on one side of the pressure relief valve.

12. A process in accordance with claim 11, wherein a volume flow of the control flow flowing through the control duct and acting on the control port of the pressure relief valve is set in the pressure control unit as a function of the permissible maximum pressure desired in the main flow duct.

13. A process in accordance with claim 11, wherein a flow resistance of the control duct is changed as a function of the permissible maximum pressure desired for the main flow duct.

14. A process in accordance with claim 11, wherein a pressure surge-free stream of a gas and/or medical air is fed to a laboratory apparatus and/or to a medical device.

* * * * *